United States Patent [19]

Igaue et al.

[11] Patent Number: 5,665,083
[45] Date of Patent: Sep. 9, 1997

[54] ABSORBENT MEMBER FOR ABSORBENT ARTICLE

[75] Inventors: Takamitsu Igaue; Tsutomu Kido, both of Kawanoe, Japan

[73] Assignee: Uni-Charm Corporation, Ehime-ken, Japan

[21] Appl. No.: 631,117

[22] Filed: Apr. 12, 1996

Related U.S. Application Data

[63] Continuation of Ser. No. 272,316, Jul. 8, 1994, abandoned.

[30] Foreign Application Priority Data

Jul. 15, 1993 [JP] Japan ................................. 5-175258

[51] Int. Cl.$^6$ .............................. A61F 13/15; A61F 13/20
[52] U.S. Cl. ........................... 604/370; 604/372; 604/378; 604/383; 428/137
[58] Field of Search ............................. 604/358, 365, 604/366, 370, 372, 378, 385.1, 381–383; 428/137, 247, 255, 304.4, 306.6, 314.4

[56] References Cited

U.S. PATENT DOCUMENTS 3,587,579  6/1971  Sabee .
3,994,299  11/1976  Karami ................................. 604/370
4,184,902  1/1980  Karami ................................. 604/383
4,690,679  9/1987  Mattingly, III et al. .
4,762,520  8/1988  Wallstrom ............................ 604/370

FOREIGN PATENT DOCUMENTS

0 467 409  1/1992  European Pat. Off. .
0 523 719  1/1993  European Pat. Off. .
51-103545  9/1976  Japan .
57-82504  5/1982  Japan .
1540474  2/1979  United Kingdom .
2055586  3/1981  United Kingdom .
2262235  6/1993  United Kingdom .
93/12745  7/1993  WIPO .

*Primary Examiner*—P. Zuttarelli
*Attorney, Agent, or Firm*—Lowe, Price, LeBlanc & Becker

[57] ABSTRACT

An absorbent member comprises an absorbent core, a liquid permeable covering sheet and a reticulated sheet interposed between the absorbent core and the covering sheet 11, wherein the reticulated sheet has a relatively higher open ratio over at least an inwardly facing surface of the absorbent core than over any of oppsite side regions and opposite end regions thereof.

1 Claim, 6 Drawing Sheets

ABSORBENT MEMBER FOR ABSORBENT ARTICLE

This application is a continuation of application Ser. No. 08/272,316 filed Jul. 8, 1994 now abondoned.

BACKGROUND OF THE INVENTION

The present invention relates to an absorbent member for use in absorbent articles such as disposable diapers or sanitary napkins, and further relates to a method of manufacturing such an absorbent member.

Heretofore, absorbent bodies have been widely used, which include a liquid permeable sheet such as a tissue paper for covering an absorbent core comprising fluff pulp or a mixture of fluff pulp and superabsorbent polymer. Since the fluff pulp is of fine fibers and the superabsorbent polymer is of powders or fine particles, they are usually preformed into a core of desired shape before they are covered with a tissue paper and the like to facilitate handling thereof in the course of manufacturing processes of the above-mentioned articles and also to prevent fiber flocks and particles from leaking off the articles during use thereof. For example, Japanese Kokai (unexamined) Patent No. Sho 51-103545 teaches a general matter on such a covering technique.

In general, despite that absorbent bodies are covered with a tissue paper, the absorbent bodies tend to lose their shapes as they absorb liquids which cause entanglement of pulp fibers to come loose and the tissue paper to break. This provides discomfort to users during use and difficulties of handling thereof after use. One measure to avoid such inconveniences is to improve a wet strength of the absorbent body. For instance, Japanese Kokai (unexamined) Pat. No. Sho 57-82504 proposes to prevent an absorbent body from losing its shape by covering an absorbent core comprising fluff pulp with a reticulated sheet formed of synthetic resin to form an absorbent body and thereafter securing the reticulated sheet to an inwardly facing surface of a backsheet of an article. U.S. Pat. No. 3,587,579 discloses a technique which covers fluff pulp with a reticulated sheet such as a woven fabric or a non-woven fabric of coarse meshes to form an absorbent body having improved the tensile strength. This technique also serves to prevent the absorbent body from losing its shape.

SUMMARY OF THE INVENTION

These conventional techniques all utilize a reticulated sheet. While it is preferred from a view point of an absorbing performance of the absorbent body that the reticulated sheet has a higher open ratio, it is also preferred from a view point of a protective performance of preventing the absorbent body from losing its shape that the reticulated sheet has a lower open ratio to reinforce the wet strength of the absorbent body. As such, these two performances are in a reciprocal relationship with each other. Accordingly, an attempt to obtain an absorbent body having both performances tends to fail with the result of sacrificing either of them.

The present invention is directed toward solving the above problems of the prior art and has its object to provide an absorbent member which particularly places a reticulated sheet of relatively high open ratio over a central region of an absorbent core and interposes the reticulated sheet between an absorbent core and a covering sheet for covering the absorbent core. The present invention further provides a method for manufacturing an absorbent member incorporating such a reticulated sheet.

The present invention employs the following means to solve the above problems.

(1) It is a premise of an absorbent member for an absorbent article in accordance with the present invention that the absorbent member is interposed between a liquid permeable topsheet and a liquid impermeable backsheet of the absorbent article.

Under such a premise, it is a distinguished feature of the present invention is that an absorbent member has an absorbent core, a liquid permeable covering sheet for covering at least an inwardly facing surface of the core, and a reticulated sheet formed of thermoplastic synthetic resin and interposed between the absorbent core and the covering sheet, and the reticulated sheet has a relatively higher open ratio over a central region of the inwardly facing surface than over any of opposite lateral side regions and opposite longitudinal end regions which respectively surround the central region.

In a preferred embodiment of the absorbent member, the reticulated sheet is heat-bonded to one of the absorbent core and the covering sheet. In another embodiment, the reticulated sheet is a laminated three-layer sheet which comprises a central layer sheet having a relatively higher melting point, upper and lower layer sheets having melting points lower than the melting point of the central layer.

(2) In a method for manufacturing an absorbent member in accordance with the present invention, a distinguished feature of the present method is to include at least the following steps under a premise that the absorbent member includes an absorbent core covered with a liquid permeable covering sheet and a reticulated sheet and is adapted to be interposed between a liquid permeable topsheet and a liquid impermeable backsheet of an absorbent article:

(a) a step of applying to a continuously delivered, thermoplastic synthetic resin sheet a number of slits arranged in a moving direction of the resin sheet in a predetermined patterned manner;

(b) a step of stretching the resin sheet to form the reticulated sheet having a transverse central region having a relatively high open ratio;

(c) a step of locating the central region of the reticulated sheet over a central region of an inwardly facing surface of the absorbent core to cover the absorbent core; and (d) a step of covering the absorbent core and the reticulated sheet with the covering sheet.

In a preferred embodiment of the present method, a step of heat-bonding the reticulated sheet to one of the absorbent core and the covering sheet is further included.

Even after the absorbent member including the reticulated sheet for covering the absorbent core absorbs liquids to be in a wet state, the reticulated sheet retains its strength to help preventing the absorbent member from losing its shape. The reticulated sheet has a high open ratio over the central region of the absorbent core so that an absorbing rate is not disturbed. Meanwhile, the reticulated sheet has a low open ratio over the region of the absorbent core surrounding the central region to maintain air-permeability between the absorbent core and the topsheet and also to prevent body exudates from leaking out of the absorbent core through the surrounding region of the absorbent core. Furthermore, when the reticulated sheet is heat-bonded to the absorbent core or the covering sheet for its positional fixation, it serves to restrain the movement of the absorbent core so that the shape of the absorbent member is more effectively retained.

In order to obtain such a reticulated sheet, openings are made in a transverse central area of a synthetic resin sheet so that an open ratio thereof becomes relatively higher while delivered in one direction. To this end, more slits are applied to the central area of the synthetic resin sheet than to the opposite side regions of the central region before the sheet is uniformly stretched. Alternatively, a number of slits are applied uniformly in a width direction of the resin sheet and the resin sheet is stretched so that a stretching rate is higher in the central region than in the opposite side regions thereof.

In the event that the reticulated sheet comprises a three-layer laminated sheet and a material for an intermediate sheet is selected to have a higher melting point than those of upper and lower layer sheets, the intermediate sheet is able to stay firm and is not softened excessively even at a temperature that the upper and lower layer sheets melt, so that a heat-bonding operation is facilitated.

PREFERRED EMBODIMENTS OF THE INVENTION

An absorbent member for an absorbent article and a method of manufacturing the absorbent member in accordance with the present invention will be hereinafter explained in detail with reference to the accompanying drawings.

Figure 1:
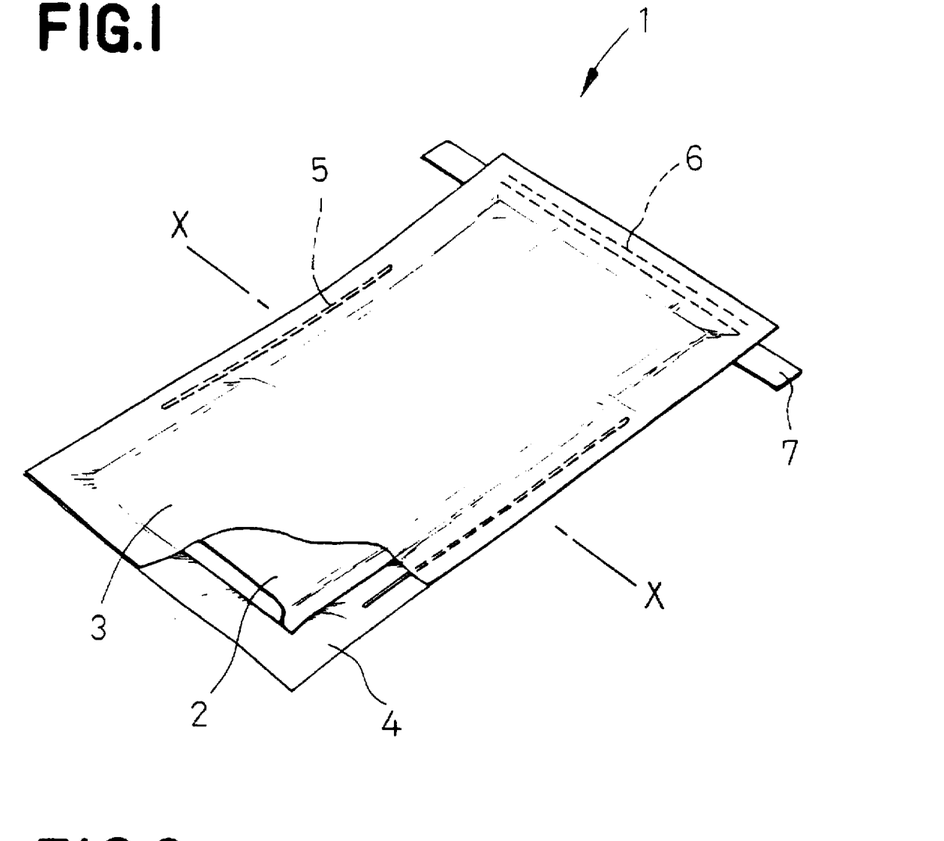
FIG. 1 is a partly cut-away perspective view of a disposable diaper.

FIG. 1 shows a partly cut-away perspective view of an absorbent article, such as a disposable diaper 1 incorporating an absorbent member 2 embodying the present invention. The disposable diaper 1 has a liquid-permeable topsheet 3, a liquid-impermeable backsheet 4, an absorbent member 2 interposed between the topsheet 3 and the backsheet 4, elastic members 5, 6 disposed respectively along leg-surrounding side edges and a waist-surrounding end edge of a rear section, and tape fasteners disposed at opposite side edges of the rear section.

Figure 2:
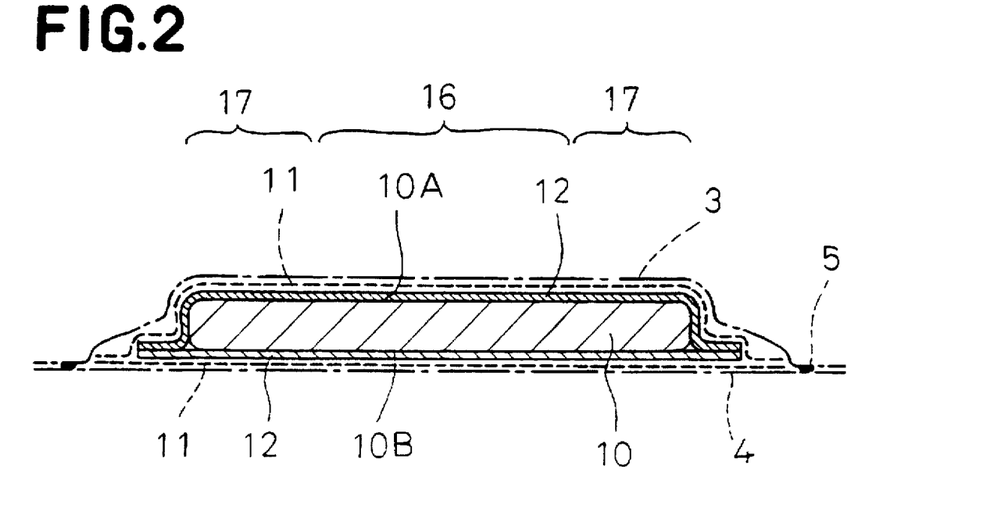
FIG. 2 is an end view taken along a line X—X of FIG. 1.

FIG. 2 is an end view taken along a line X—X of FIG. 1. The topsheet 3 and the backsheet 4 are respectively indicated by chain lines and a tissue paper 11 as will be described later is indicated by a broken line.

Figure 3:
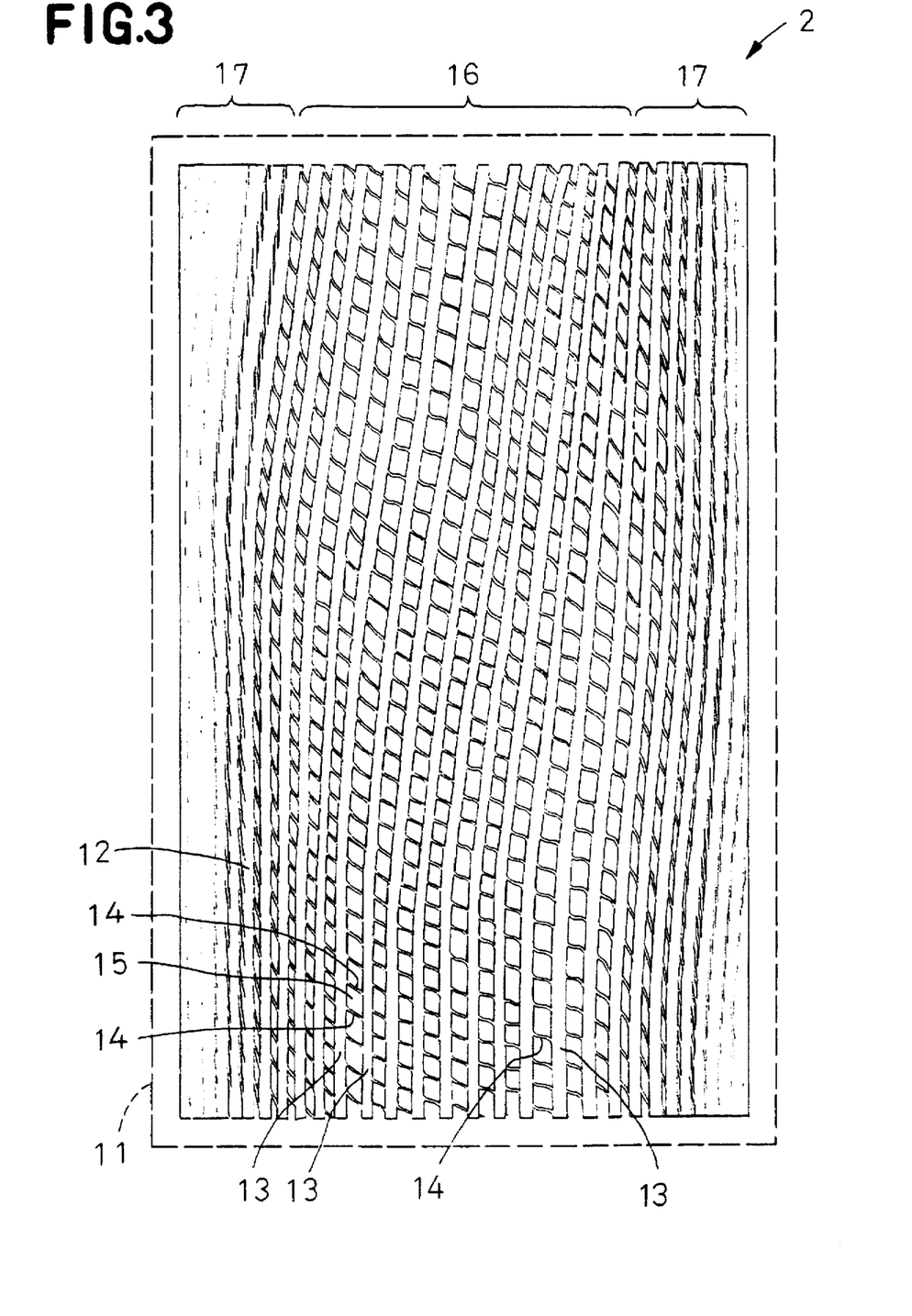
FIG. 3 is a plan view of an absorbent member.

FIG. 3 is a plan view of the absorbent member 2 incorporated in the disposable diaper 1. A peripheral profile of the tissue paper 11 is indicated therein by a broken line.

In FIGS. 2 and 3, the absorbent member 2 comprises a preshaped rectangular absorbent core 10 comprising a mixture of fluff pulp and superabsorbent polymer, a tissue paper 11 for covering the absorbent core 10, a reticulated sheet disposed between the absorbent core 10 and the tissue paper 11 for covering the absorbent core 10. Two sheets of the tissue paper 11 are provided to cover an inwardly facing surface 10A and an outwardly facing surface 10B, respectively. Those two sheets are placed upon each other outwardly of peripheral edges of the absorbent core 10 and be further adhesively secured to each other.

The reticulated sheet 12 is a laminated three-layer sheet which includes an intermediate polypropylene layer and ethylene-vinyl acetate layers integrally laminated onto upper and lower surfaces of the intermediate polypropylene layer. The reticulated sheet 12 has longitudinally extending, continuous thick (or coarse) filaments 13 and short thin (fine) filaments 14 extending transeversely from the thick filaments 13. A pair of neighboring, thin filaments 14 extends transversely between a pair of neighboring, thin filaments 14 to define an opening 15 therebetween. The thick and thin filaments 13, 14 are arranged at relatively wide intervals in a transverse central region 16 of the reticulated sheet over the inwardly facing surface 10A of the absorbent core 10 to enlarge areas of the openings 15, and therefore to provide a relatively higher open ratio. In opposite sides of the central region, any of the thick filaments 13 and the thin filaments 14 are arranged at relatively close intervals so that the openings 15 are rarely formed or define small areas, if they are formed, to provide a low open ratio.

Similarly to the tissue paper 11, two sheets of the reticulated sheet 12 are provided to cover an inwardly facing surface 10A and an outwardly facing surface 10B, respectively. These two sheets extend outwardly from the peripheral edges of the absorbent core 10 to define marginal portions in which the upper and lower ethylene-vinyl acetate layers are fusively secured to each other and further to the tissue paper 11 and the absorbent core 10 in an intermittent manner. The openings 15 of the reticulated sheet 12 are through holes to permit body exudates discharged over the topsheet 3 to move therethrough toward the absorbent core 10. The thick and thin filaments 13, 14 are illustrated to somewhat slant with respect to transverse and longitudinal directions, respectively, which depend upon a manufacturing method regarding the reticulated sheet 12 as described hereinafter.

The disposable diaper 1 incorporating the absorbent member 2 is able to retain its shape against any vigorous movements of a user during use because the absorbent member 2 serves to restrain the free movements of the absorbent core 10 by the provision of the reticulated sheet that covers and is fusively secured to the absorbent core 10. In addition, the diaper 1 retains its shape even after its absorption of body exudates since the strength of the reticulated sheet 12 does not fall even in a wet condition. The reticulated sheet 12 has a high open ratio in its central region 16 where body exudates are heavily localized so that it does not provide an adverse effect of slowing a body exudates absorbing rate. On the other hand, the reticulated sheet 12 has opposite side regions 17 of lower open ratio where the thick and thin filaments 13, 14 are closely spaced from each other so that the area of the reticulated sheet 12 fusively secured to the absorbent core 10 is enlarged. This serves to restrain the movement of the absorbent core 10 over a large area so that the shape retaining effect of the reticulated sheet is enhanced, and to improve the tensile strength of the absorbent core 10, and further to prevent the body exudates once absorbed from leaking out of side portions of the absorbent core 10. The presence of the openings 15 in the opposite side regions 17 still permits air to pass between the absorbent core 10 and the topsheet 3 so that the diaper 1 can not be steamed. In order to bring about these effects, it is preferred that the reticulated sheet 12 has an open ratio of 40–98% in its central region 16 and an open ratio of 5–60% in its opposite side regions 17, with its open ratio in the central region 16 being always maintained to be higher than that in the opposite side regions 17.

Figure 4:
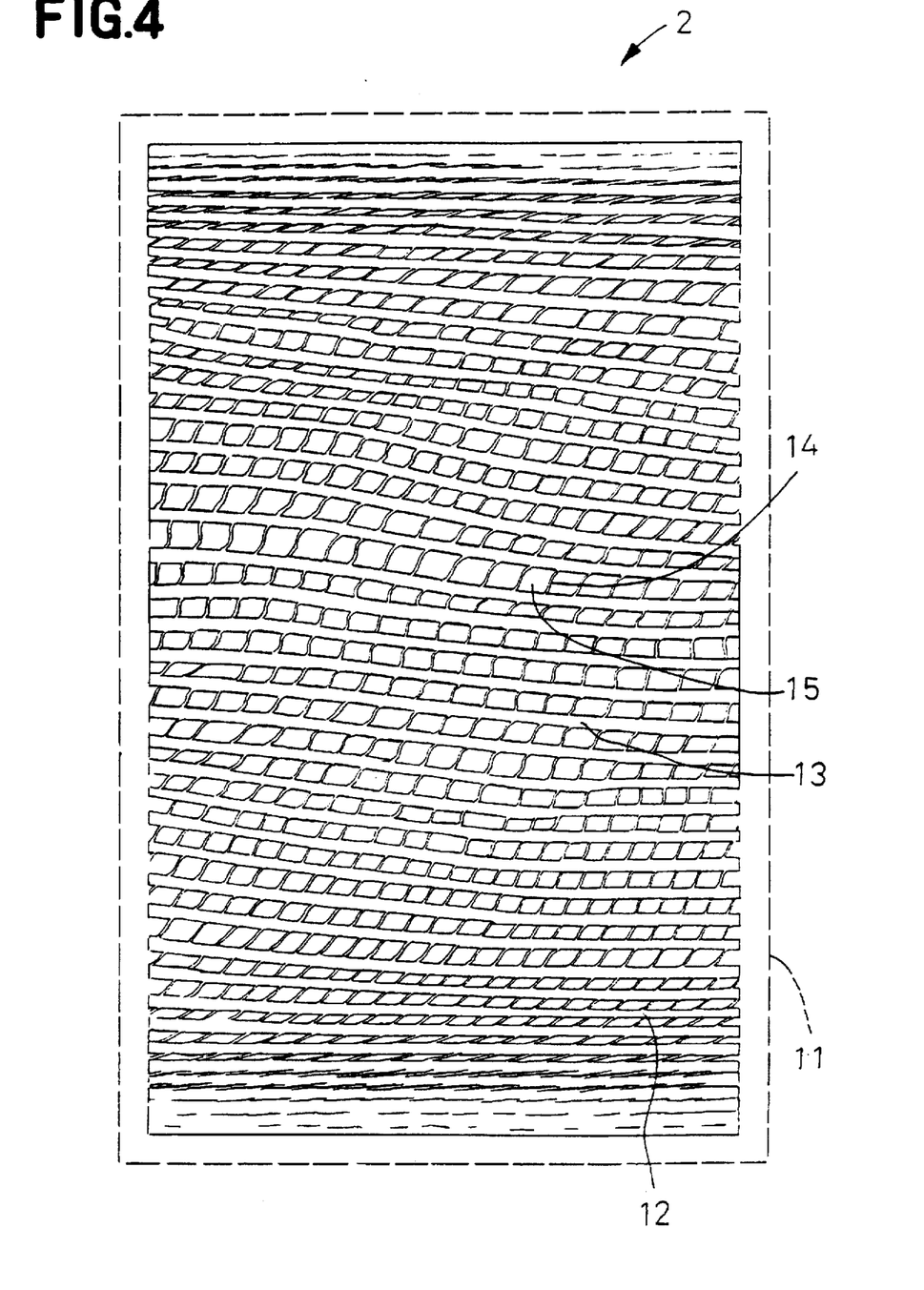
FIG. 4 is a plan view of an absorbent member, as similar to that of FIG. 3, illustrating another embodiment of the reticulated sheet.

FIG. 4 is a plan view of the absorbent article 2 as similar to the one in FIG. 2. However, the reticulated sheet 12 is turned by 90 degrees. By doing so, the transverse tensile strength of the absorbent member 2 can be improved and the leakage of body exudates from opposite end regions thereof is prevented.

It should be noted here that two sheets of the retticulated sheet 12 may be placed upon each other in the crossed state of the thick filaments 13, though not illustrated here. Where the reticulated sheets are placed so, they will have a low open ratio both in the opposite side regions and in the opposite end regions.

Figure 5:
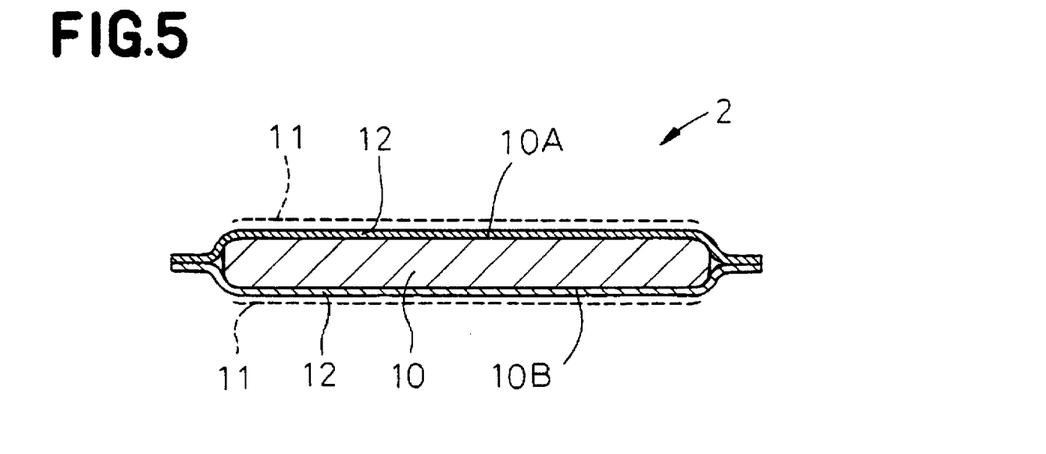
FIG. 5 is an end view illustrating one embodiment of the absorbent member.
Figure 6:
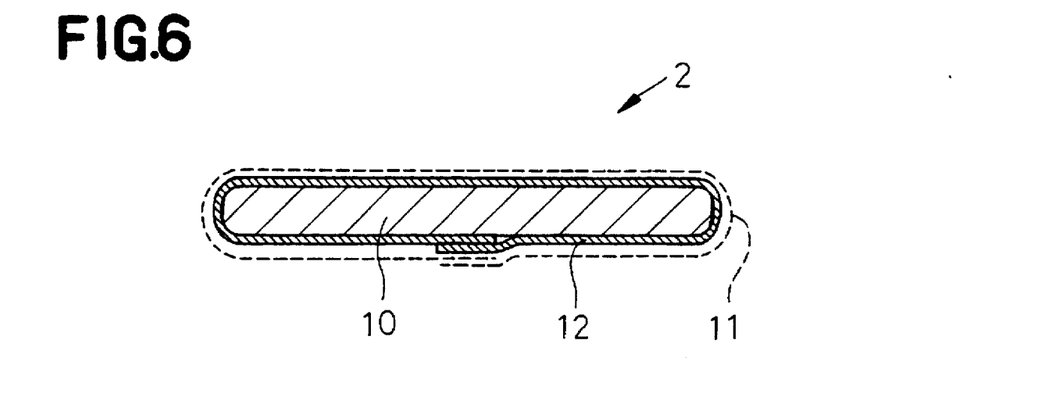
FIG. 6 is an end view illustrating another embodiment of the absorbent member which is different from that of FIG. 5.
Figure 7:
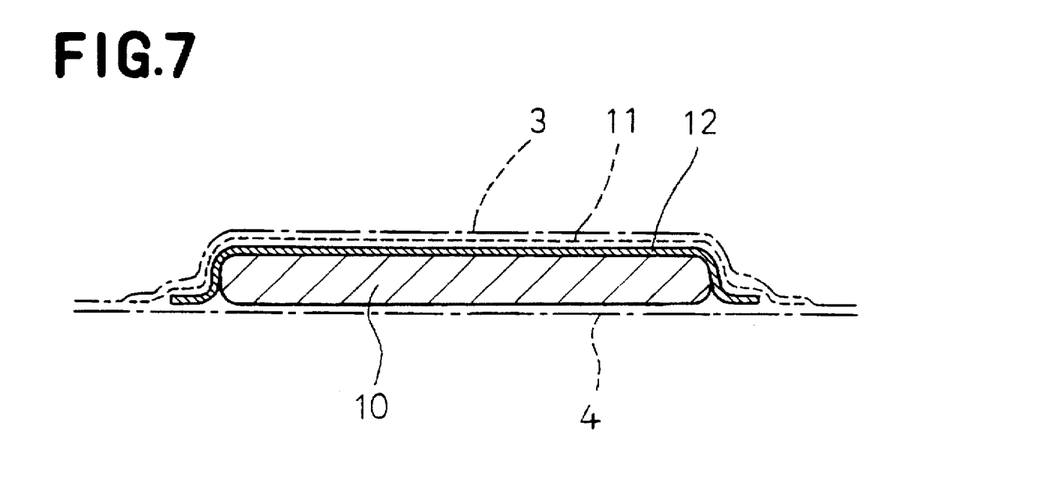
FIG. 7 is an end view illustrating still another embodiment of the absorbent member which is different from those of FIGS. 5 and 6.

FIGS. 5 through 7 are end views respectively illustrating various embodiments of the absorbent member 2 as similar to that of FIG. 2. In FIG. 5, the tissue paper 11 has a width smaller than that of the reticulated sheet 12. The reticulated sheet 12 has small openings 15 at opposite side edges of the absorbent core 10. If fluff pulp and superabsorbent polymer contained in the absorbent core 10 are not likely to leak through the reticulated sheet 12, the tissue paper 11 may be required to cover only the inwardly or outwardly facing surfaces 10A, 10B of the absorbent core 10, or only the central region thereof. In FIG. 6, the reticulated sheet 12 and the tissue paper 11 are both wound around the absorbent core 10. In FIG. 7, the reticulated sheet 12 and the tissue paper 11 cover the absorbent core 10 placed on the backsheet 4. They are further covered with the topsheet 3. The reticulated sheet 12 may be secured to the backsheet 4 along the opposite side edges of the absorbent core 10 and, if necessary, along the outer edges thereof to prevent the absorbent core 10 from losing its shape.

Figure 8:
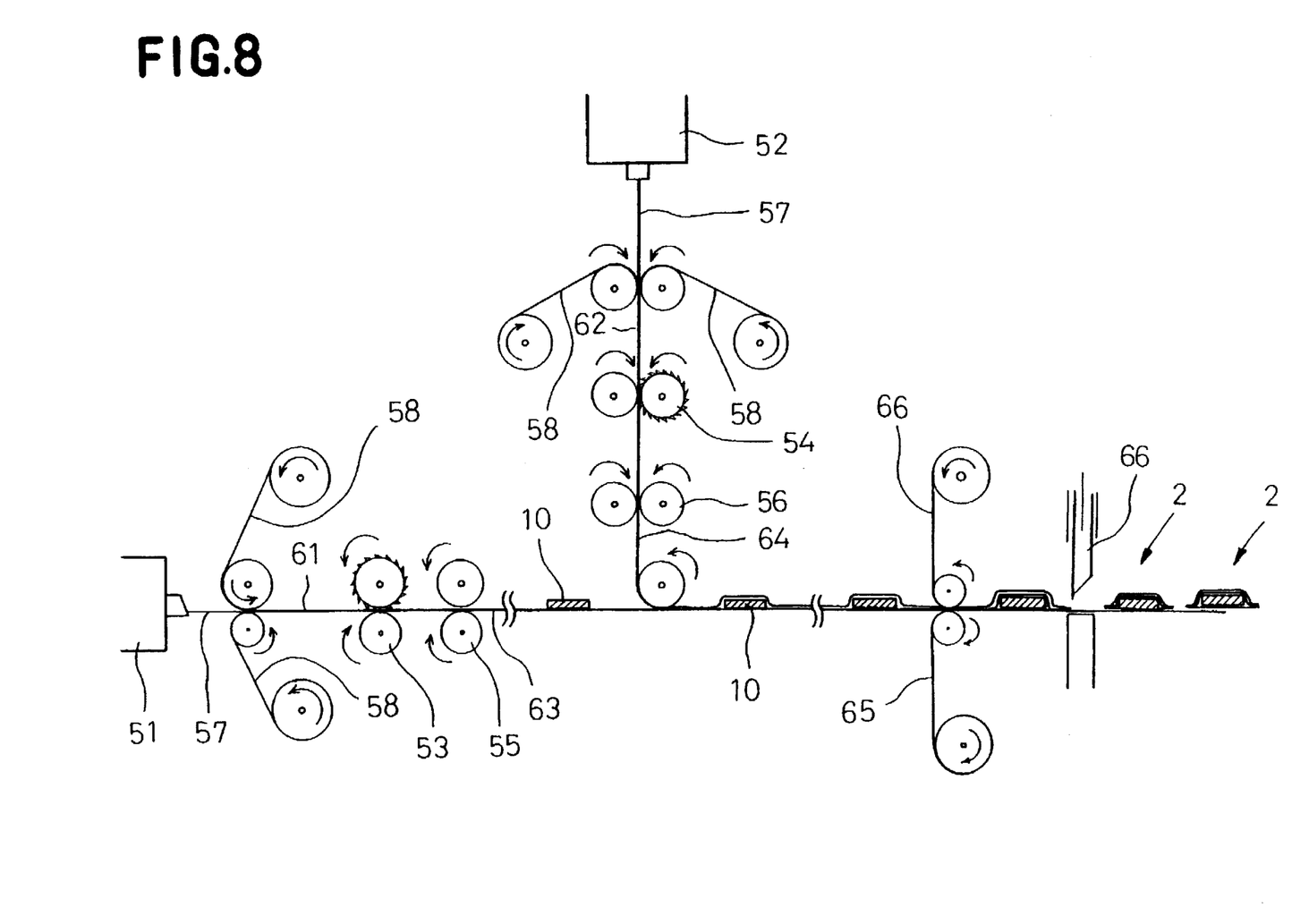
FIG. 8 is a schematic diagram of processes to be used in manufacturing the absorbent member.

FIG. 8 representatively shows a schematic diagram of processes to be used in manufacturing the absorbent member 2. In the processes, there are provided first and second extruders 51, 52 to form two reticulated sheets 12 for respectively covering the inwardly and outwardly facing surfaces of the absorbent core 12, first and second slitters 53, 54, and first and second tenters 55, 56. The first extruder 51 forms a polypropylene sheet 57 having opposite surfaces to which ethylene-vinyl acetate sheets 58 are laminated to form a first three-layer sheet 61. The second extruder 52 forms the polypropylene sheet 57 having opposite surfaces to which ethylene-vinyl acetate sheets 58 are laminated to form a second three-layer sheet 62. The first and second slitters 53, 54 apply slitting respectively to the first and second three-layer sheets 61, 62 to form therein slits extending in moving directions thereof in predetermined patterns. They are subsequently stretched at predetermined rates respectively by the first and second tenters 55, 56 so that the slits therein are opened to define the apertures 15. These sheets having apertures 15 form first and second continuous reticulated sheets 63, 64 which are substantially identical to each other.

The discrete absorbent cores 10 preformed in another process (not shown) are then placed on the first continuous reticulated sheet 63 at predetermined intervals. The second continuous reticulated sheet 64 is introduced thereover and is then bonded to the first continuous reticulated sheet 63 along the side edges or four peripheries of the absorbent core 10. The first and second continuous tissue papers 65, 66 are fed on the first and second continuous reticulated sheets 63, 64, respectively and are compressively placed upon or adhesively secured to each other along the side edges or four peripheries of the absorbent core 10. The cutter 66 then severes the assembly into separate individual absorbent cores 10 so that individual absorbent members 2 are obtained.

Figure 9A:
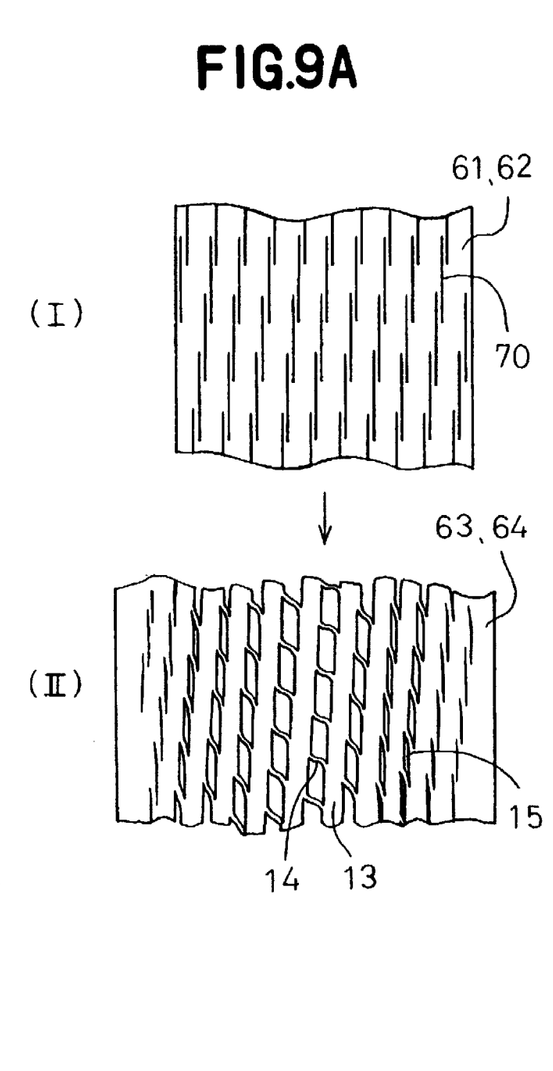
FIG. 9 is fragmentary plan views of thermoplastic resin sheets illustrating embodiments of slit formation (A) and (B).
Figure 9B:
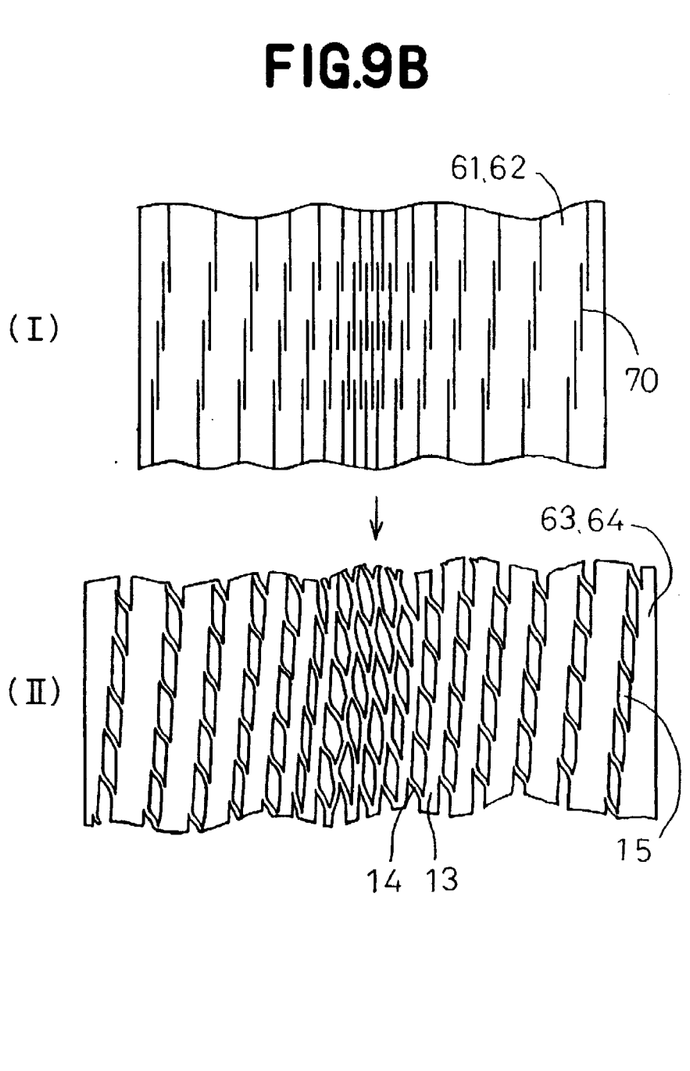

FIG. 9 shows plan views exemplarily illustrating patterned applications of longitudinally long slits 70 in the first and second three-layer sheets 61, 62 before and after stretching by (A) and (B) wherein (1) and (2) show the states thereof before and after stretching is made, respectively. In FIG. 9(A), the slits 70 in the first and second three-layer sheets 61, 62 are uniformly distributed in a transverse direction thereof. In FIG. 9(B), the slits 70 in the first and second three-layer sheets 61, 62 are closely distributed in the transverse central regions thereof.

The first and second three-layer sheets 61, 62 in the (A) state are stretched in the stretching process of FIG. 8 so that relatively higher stretching rates are given in the central regions thereof. The first and second three-layer sheets 61, 62 in the (B) state are stretched so that the uniform stretching rate is given transversely thereof. Such stretching results in that the first and second continuous reticulated sheets 63, 64 and the reticulated sheet 12 obtained therefrom respectively have the higher open ratios in the central regions thereof than in the opposite side regions thereof. When the slit patterns as illustrated in (1) are formed in the three-layer sheets 61, 62, the slant angles of the longitudinal and transverse thick and thin filaments 13, 14 created in (II) are changed in accordance with the applied stretching rates.

The first and second continuous reticulated sheets 63, 64 can be fusively secured to the first and second continuous tissue papers 65, 66 and the absorbent cores at appropriate locations in the processes of FIG. 8. Only a slight heating is required to fusively secure them since each of the reticulated sheets 63, 64 has in its opposite surfaces highly heat-sealable ethylene-vinyl acetate layers. Furthermore, the use of polypropylene layer as the intermediate layer permits the first and second reticulated sheets 63, 64 to remain firm even at temperatures where ethylene-vinyl acetate layers melt, and therefore facilitating the securement operations.

When incorporated in the diaper 1, it becomes important that the reticulated sheet 12 has a high open ratio in the site to which body exudates are discharged. It is preferred that the reticulated sheet 12 has low open ratios in the other sites including a site facing toward the backsheet 4 so that the tensile strength of the absorbent core 10 is not sacrificed and the effective, body exudates leakage protection is provided while the diaper 1 is hardly steamed. Different qualities or characteristics can be given to the first and second reticulated sheet 63, 64 for their respective intended uses.

A typical example of the reticulated sheet 12 is a three-layer sheet having a thickness in the range of 30–200 microns which comprises a polypropylene sheet having a thickness in the range of 10–60 microns and ethylene-vinyl acetate sheets each having a thickness in the range of 10–80 microns. The use of the polypropylene sheet and ethylene-vinyl acetate sheets which have molecular orientations in the directions they are fed facilitates formation of the slits 70 and apertures 15. A product preformed of fluff pulp or a mixture of fluff pulp and superabsorbent polymer can be used for the absorbent core 12.

The absorbent member of the present invention includes the reticulated sheet formed of thermoplastic resins to cover the absorbent core so that it is able to retain its shape. The reticulated sheet has a high open ratio over a central region of the absorbent core so that it does not disturb a body exudates absorbing rate, and low open ratios in regions surrounding the central region of the absorbent core so that the absorbent core and the covering sheet can be fusively secured to each other over a large area. The large securement area thus obtained serves to restrain movements of the absorbent core and to further improve a protective effect of preventing the abosorbent core from losing its shape.

The slit formation in a continuously delivered thermoplastic resin sheet and subsequent stretching facilitate manufacture of the reticulated sheet having selected open ratios.

The reticulated sheet serves to prevent body exudates from leaking through peripheral regions of the absorbent core.

What is claimed is:

1. An absorbent member interposed between a liquid permeble topsheet and a liquid impermeable backsheet of an absorbent article, said absorbent member comprising:

an absorbent core;

a liquid permeable covering sheet for covering at least a body facing surface of said absorbent core; and a reticulated sheet interposed between said absorbent core and said covering sheet, and having a relatively higher open ratio over a central region of said body facing surface than over any of opposite lateral side regions and opposite longitudinal end regions respectively surrounding said central region; wherein said reticulated sheet is a laminated three-layer sheet which comprises a central layer sheet having a relatively higher melting point, upper and lower layer sheets having melting points lower than the melting point of said central layer.

* * * * *